US006775850B1

(12) United States Patent
Grilliot et al.

(10) Patent No.: US 6,775,850 B1
(45) Date of Patent: Aug. 17, 2004

(54) PROTECTIVE COMBINATION COMPRISING FACE MASK, PROTECTIVE GARMENT HAVING HOOD, AND INFLATABLE SEAL, FOR FIREFIGHTER OR EMERGENCY WORKER

(75) Inventors: William L. Grilliot, Dayton, OH (US); Mary I. Grilliot, Dayton, OH (US)

(73) Assignee: Morning Pride Manufacturing, L.L.C., Dayton, OH (US)

( * ) Notice: Subject to any disclaimer, the term of this patent is extended or adjusted under 35 U.S.C. 154(b) by 0 days.

(21) Appl. No.: 10/461,999

(22) Filed: Jun. 12, 2003

(51) Int. Cl.[7] ............................ A42B 1/08; A61F 9/02; A62B 17/00

(52) U.S. Cl. ........................... 2/424; 2/5; 2/173; 2/205; 2/428; 128/201.23; 128/201.29; 128/206.24

(58) Field of Search ............................ 2/424, 205, 428, 2/5, 410, 202, 6.3, 6.7, DIG. 3, 173, 2.11, 2.14, 2.15, 901, 457, 458; 128/200.28, 201.22, 201.24, 201.25, 206.23, 201.23, 201.29, 206.24

(56) References Cited

U.S. PATENT DOCUMENTS

| | | | | |
|---|---|---|---|---|
| 1,930,399 A | | 10/1933 | Stelzner | |
| 2,935,985 A | | 5/1960 | Andrews et al. | |
| 2,978,708 A | | 4/1961 | Williams et al. | |
| 3,438,060 A | | 4/1969 | Lobelle et al. | |
| 4,174,710 A | | 11/1979 | Pampuch | |
| 4,352,353 A | | 10/1982 | Bolton et al. | |
| 5,647,059 A | * | 7/1997 | Uglene et al. | 2/2.15 |
| 6,266,828 B1 | | 7/2001 | Corsini | |
| 6,328,031 B1 | | 12/2001 | Tischer et al. | |
| 6,478,025 B1 | | 11/2002 | Yort et al. | |
| 6,578,572 B2 | | 6/2003 | Tischer et al. | |
| 2002/0092522 A1 | | 7/2002 | Fabin | |

FOREIGN PATENT DOCUMENTS

| | | |
|---|---|---|
| GB | 2133274 A | 7/1984 |

* cited by examiner

*Primary Examiner*—Rodney M. Lindsey
(74) *Attorney, Agent, or Firm*—Wood, Phillips, Katz, Clark & Mortimer

(57) ABSTRACT

In a protective combination wearable by a firefighter or by an emergency worker, a face mask has a face-conformable gasket defining an outwardly opening trough. Further, a protective garment has a hood, which has a peripheral edge and which defines a tubular hem along the peripheral edge. Moreover, an inflatable tube, which extends through the tubular hem, is adapted to form a seal between the face-conformable gasket and the peripheral edge of the hood, when inflated so as to press the tubular hem along the peripheral edge of the hood into the outwardly opening trough, whereby to provide a seal between the face mask and the hood.

3 Claims, 1 Drawing Sheet

PROTECTIVE COMBINATION COMPRISING FACE MASK, PROTECTIVE GARMENT HAVING HOOD, AND INFLATABLE SEAL, FOR FIREFIGHTER OR EMERGENCY WORKER

TECHNICAL FIELD OF THE INVENTION

This invention pertains to a protective combination comprising a face mask and a protective garment having a hood, as wearable by a firefighter or by an emergency worker. This invention contemplates that the protective combination also comprises an inflatable seal between the face mask and the hood.

BACKGROUND OF THE INVENTION

Commonly, when called upon to deal with hazardous chemical or biological materials, a firefighter or an emergency worker wears a face mask, which is connected to a self-contained breathing apparatus (SCBA) or to a respirator having an air filter, and a protective garment, such as protective coveralls, which has a hood. It has been known, heretofore, to use fluid-tight tape to form a fluid-tight seal between the face mask and the hood.

Commonly, a face mask to be thus worn has a transparent window and a rubbery, face-conformable gasket around the transparent window. Commonly, the rubbery, face-conforming gasket has an outwardly opening trough, which bounds the transparent window. Such a face mask having such a gasket having such a trough is available commercially from numerous.

SUMMARY OF THE INVENTION

This invention provides, in a protective combination wearable by a firefighter or by an emergency worker, a face mask, a protective garment, which has a hood, and an inflatable seal between the face mask and the hood.

Preferably, in the protective combination, the face mask has an outwardly opening trough, the protective garment has a hood having a peripheral edge, and an inflatable tube is provided, which is adapted to form a fluid-tight seal between the face mask and the hood, when the inflatable tube is inflated so as to press the peripheral edge of the hood into the outwardly opening trough, whereby to provide a seal between the face mask and the hood. Preferably, the face mask has a face-conformable gasket, which has the outwardly opening trough. Preferably, the peripheral edge of the hood has a tubular hem, through which the inflatable tube extends.

In a preferred embodiment of this invention, the protective combination comprises a face mask, which has a face-conformable gasket defining an outwardly opening trough, a protective garment, which has a hood having a peripheral edge and defining a tubular hem along the peripheral edge, and an inflatable tube, which extends through the tubular hem and which is adapted to form a fluid-tight seal between the face-conformable gasket and the peripheral edge of the hood, when the inflatable tube is inflated so as to press the tubular hem along the peripheral edge of the hood into the outwardly opening trough, whereby to provide a seal between the face mask and the hood.

DETAILED DESCRIPTION OF THE ILLUSTRATED EMBODIMENT

Figure 1:
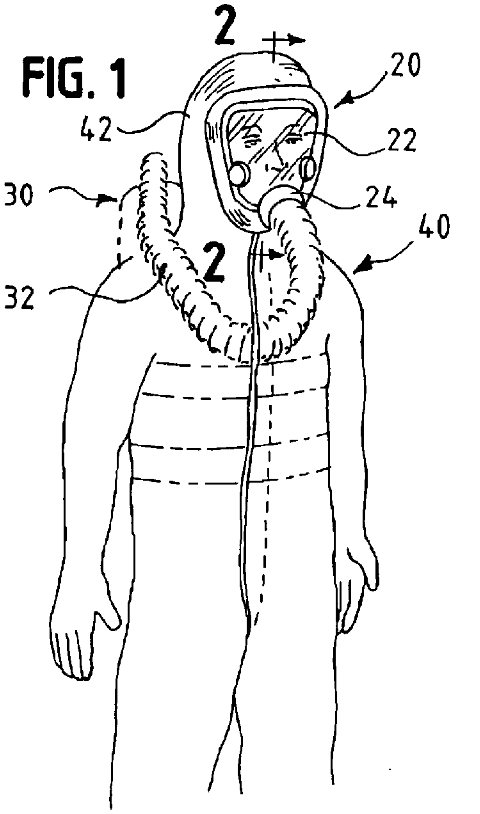
FIG. 1 is a fragmentary, perspective of a person, such as a firefighter or an emergency worker, who is wearing a protective combination comprising a face mask, a protective garment with a hood, and an inflatable tube and embodying this invention.

As illustrated, a protective combination worn by a firefighter or by an emergency worker comprises a face mask 20, which is connected to a self-contained breathing apparatus (SCBA) 30 via a flexible hose 32, a protective garment 40, which has a hood 42, and an inflatable tube 50, which provides an inflatable seal between the face mask 20 and the hood 42.

As illustrated, the face mask 20 has a transparent window 22, a fitment 24, by which the flexible hose 32 is connected to the face mask 20, at the transparent window 22, and a rubbery, face-conformable gasket 26, which bounds the transparent window 22 and which defines an outwardly opening trough 28. Except as illustrated and described herein, details of the face mask 20 are outside the scope of this invention and can be readily supplied by a person having ordinary skill in the art.

The protective garment 40 is made from sheets of fluid-impervious films, fabrics, or laminates. Similar protective garments are exemplified in U.S. Pat. Nos. 4,272,851, 4,864,654, and 6,364,980, which disclose suitable films, fabrics, and laminates and the disclosures of which are incorporated herein by reference. As illustrated, the protective garment 40 is provided with a fluid-tight zipper 44 for opening and closing the protective garment 40. Except as illustrated and described herein, details of the protective garment 40 are outside the scope of this invention and can be readily supplied by a person having ordinary skill in the art.

The hood 42 has a peripheral edge 46, along which the hood 42 has a tubular hem 48. The inflatable tube 50, which is made from a synthetic rubber, extends through the tubular hem 48 and is inflatable via a valve 52, which projects outwardly through a hole 54 in the tubular hem 48, so as to fill the tubular hem 48 snugly. When the protective garment 40 is closed completely, via the fluid-tight zipper 44, the opposite ends 56 of the tubular hem 48 are drawn together, whereby the opposite ends 58 of the inflatable tube 50 are drawn together.

Figure 3:
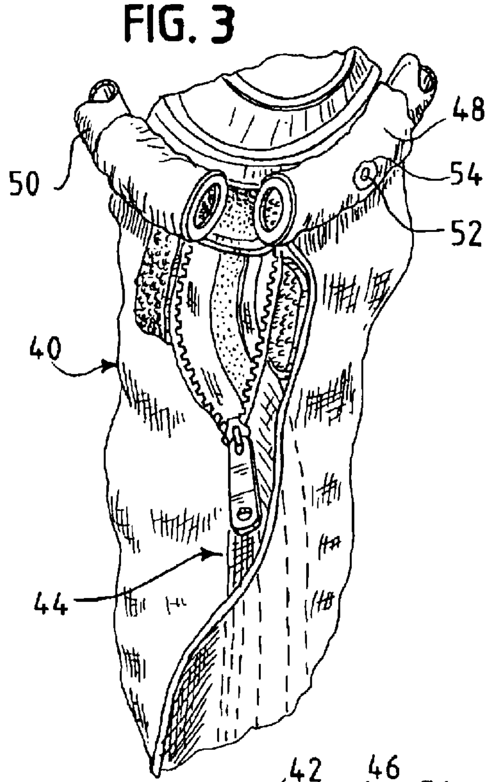
FIG. 3, on a similar scale, is a fragmentary, front view of the protective combination, as illustrated in FIG. 1, except that the protective garment is not closed completely and except that the ends of the inflatable tube are not drawn together.
Figure 2:
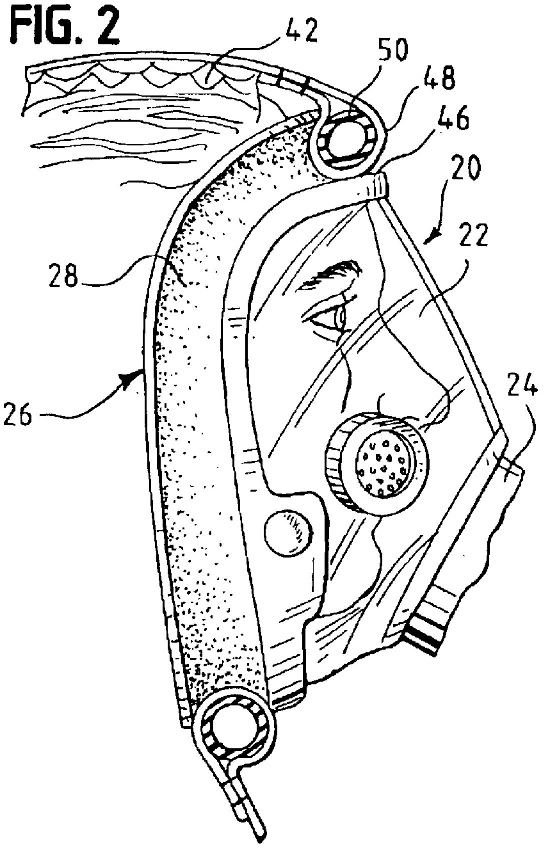
FIG. 2, on a larger scale, is a fragmentary, sectional view of the protective combination, as taken along line 2—2 of FIG. 1, in a direction indicated by arrows.
Figure 4:
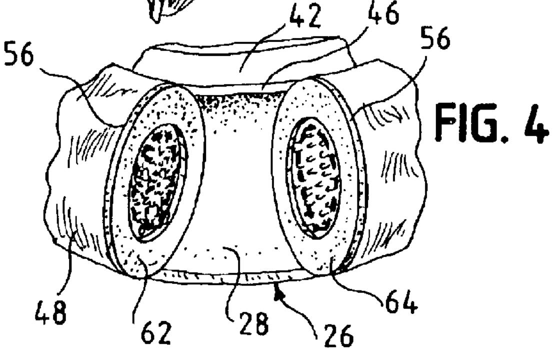
FIG. 4 is an enlarged detail, as taken from FIG. 3.
Figure 5:
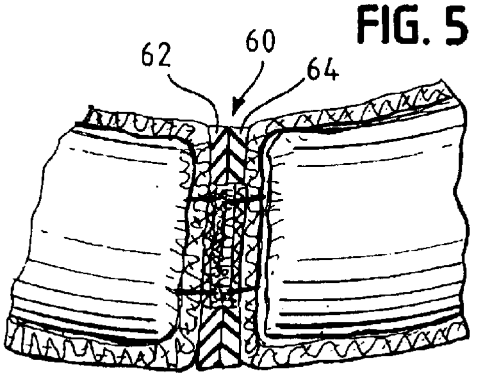
FIG. 5 is a similar detail, as taken after the protective garment has been closed completely and the ends of the inflatable tube have been drawn together.

As illustrated in FIGS. 3, 4, and 5, a hook-and-loop fastener 60 comprising a hook-faced annulus 62 attached to one said end 56 of the tubular hem 48 and comprising a loop-faced annulus 64 attached to the other end 56 of the tubular hem 48 is provided for attaching the opposite ends 56 of the tubular hem 48 detachably to each other, when the protective garment 40 is closed completely, via the fluid-tight zipper 44. Other means may be alternatively provided for a similar function.

The tubular hem 48, through which the inflatable tube 50 extends, fits into and along the outwardly opening trough 28.

Thus, when the inflatable tube 50 is inflated so as to fill the tubular hem 48 snugly, the inflated tube 50 presses the tubular hem 48 into the outwardly opening trough 28, whereby to form a seal, which may be a fluid-tight seal, between the face mask 20 and the hood 42.

What is claimed is:

1. A protective combination wearable by a firefighter or by an emergency worker, the protective combination comprising a face mask, which has an outwardly opening trough, a protective garment, which has a hood having a peripheral edge, and an inflatable tube, which is adapted to form a seal between the face mask and the hood, when the inflatable tube is inflated so as to press the peripheral edge of the hood into the outwardly opening trough, whereby to provide a seal between the face mask and the hood.

2. A protective combination wearable by a firefighter or by an emergency worker, the protective combination comprising a face mask, which has a face-conformable gasket defining an outwardly opening trough, a protective garment, which has a hood having a peripheral edge, and an inflatable tube, which is adapted to form a seal between the face-conformable gasket and the peripheral edge of the hood, when the inflatable tube is inflated so as to press the peripheral edge of the hood into the outwardly opening trough, whereby to provide a seal between the face mask and the hood.

3. A protective combination wearable by a firefighter or by an emergency worker, the protective combination comprising a face mask, which has a face-conformable gasket defining an outwardly opening trough, a protective garment, which has a hood having a peripheral edge and defining a tubular hem along the peripheral edge, and an inflatable tube, which extends through the tubular hem and which is adapted to form a seal between the face-conformable gasket and the peripheral edge of the hood, when the inflatable tube is inflated so as to press the tubular hem along the peripheral edge of the hood into the outwardly opening trough, whereby to provide a seal between the face mask and the hood.

* * * * *

UNITED STATES PATENT AND TRADEMARK OFFICE

CERTIFICATE OF CORRECTION

PATENT NO. : 6,775,850 B1 Page 1 of 1
DATED : August 17, 2004
INVENTOR(S) : William L. Grilliot and Mary I. Grilliot It is certified that error appears in the above-identified patent and that said Letters Patent is hereby corrected as shown below:

Column 1,
Line 32, after "numerous" insert -- sources --.

Signed and Sealed this

Thirtieth Day of November, 2004

JON W. DUDAS
*Director of the United States Patent and Trademark Office*